United States Patent [19]

Hoppough

[11] Patent Number: 4,653,493
[45] Date of Patent: Mar. 31, 1987

[54] VENTILATOR UNIT EXHALATION CONTAMINATION CONTROL DEVICE

[76] Inventor: John M. Hoppough, 712 W. Cass, Greenville, Mich. 48838

[21] Appl. No.: 699,924

[22] Filed: Feb. 8, 1985

[51] Int. Cl.$^4$ .............................................. A61M 16/00
[52] U.S. Cl. ........................... 128/202.22; 128/205.12; 128/910
[58] Field of Search .............. 128/910, 205.19, 205.29, 128/205.12, 205.17, 205.24, 201.28, 201.29, 205.18, 202.22, 203.28

[56] References Cited

U.S. PATENT DOCUMENTS

| 3,481,333 | 12/1969 | Garrison | 128/201.28 |
| 3,867,936 | 2/1975 | Kelley | 128/205.12 |
| 4,188,946 | 2/1980 | Watson et al. | 128/910 |
| 4,291,689 | 9/1981 | Hay | 128/910 |
| 4,299,215 | 11/1981 | Anon | 128/910 |
| 4,538,605 | 9/1985 | Gedeon et al. | 128/910 |

FOREIGN PATENT DOCUMENTS 2052270  1/1981  United Kingdom ................ 128/910

OTHER PUBLICATIONS

Air Products and Chemicals, Inc., *Foregger Hospital Equipment* catalog, 4/1975; Form No. 4DF.
*Respiratory Therapy Products*, by Instrumentation Industries Inc. catalog, p. 15.
*Ohio Anesthesia and Anesthesia Machine Accessories*, Ohio Medical Products catalog, pp. 14–15.
Suggested filter location demonstration sheets by Pall Biomedical Products Corporation, FIGS. 1–6.
*The Pall Breathing Circuit Filter* brochure.
*Pall Breathing Circuit Filter* three ring binder sheet.
Dyer & Peterson, *How Far do Bacteria Travel from the Exhalation Valve of IPPB Equipment?*, 51 Anesthesia and Analgesia, Jul.–Aug., p. 516 (1972).
Flournoy, Plumlee & Steffee, *Volume Ventilator as a Vehicle of Airborne Bacterial Contamination from Patients*, 25 Respiratory Care, Jul., p. 742 (1980).
Duberstein & Howard, *Sterile Filtration of Gases: A Bacterial Aerosol Challenge Test*, 32 Journal of the Parenteral Drug Ass., Jul.–Aug., p. 192, (1978).
Irwin et al., *An Outbreak of Acinetobacter Infection Associated with the Use of a Ventilator Spirometer*, 25 Respiratory Care, Feb., p. 232 (1980).
Malecka-Griggs & Reinhardt, *Direct Dilution Sampling, Quantitation, and Microbial Assessment of Open–System Ventilation Circuits in Intensive Care Units*, 17 Journal of Clinical Microbiology, May, p. 870 (1983).
Craven, Goularte & Make, *Contaminated Condensate in Mechanical Ventilator Circuits*, 129 Am. Rev. Respir. Dis., p. 625 (1984).
Ahlgren, Chapel & Dorn, *Pseudomonas aeruginosa Infection Potential of Oxygen Humidifier Devices*, 22 Respiratory Care, Apr., 383 (1977).
Escobar & Aldrete, *Bacteria Filters for Anesthesia Apparatus*, Anesthesiology Review, Jul., p. 25a (1977).
Helms et al., *Legionnaires' Disease Associated with a Hospital Water System: A Cluster of 24 Nosocomial Cases*, 99 Annals of Internal Medicine, p. 172 (1983).
Witek & Schachter, *Air Pollution and Respiratory Health*, 28 Respiratory Care, Apr., p. 442 (1983).
Williams & Aber, *Oropharyngeal Colonization with Aerobic Gram–Negative Bacilli in Respiratory Therapists: Period Prevalence*, 26 Respiratory Care, Feb., p. 127 (1981).
Witek et al., *The Acquired Immune Deficiency Syndrome (AIDS): Current Status and Implications for Respiratory Care Practitioners*, 29 Respiratory Care, Jan., p. 35 (1984).
Zuravleff et al., *Legionella pneumophila Contamination of a Hospital Humidifier*, 128 Am. Ref. Respir. Dis., p. 657 (1983).
Frame, *Acute Infectious Pneumonia in the Adult*, 28 Respiratory Care, Jan., p. 100 (1983).

Primary Examiner—Henry J. Recla
Attorney, Agent, or Firm—Price, Heneveld, Cooper, DeWitt & Litton

[57] ABSTRACT

A ventilation contamination control device for use on the expiratory line of a ventilator unit. The device couples to a contained vacuum source to provide a closed system that does not require the continuous, direct filtration of exhalation from the patient. The device includes a housing on which a flexible exhalation containment bag and a unidirectional check valve are mounted. The check valve permits inward atmospheric air flow during low exhalation periods but prevents outward contaiminated air flow. A bacteria filter unit is mounted on the housing to provide a filtered vent to the atmosphere in the event that the vacuum source or the check valve become obstructed or fail. An audible signal responds to such a failed condition.

14 Claims, 4 Drawing Figures

VENTILATOR UNIT EXHALATION CONTAMINATION CONTROL DEVICE

BACKGROUND OF THE INVENTION

The present invention relates to contamination control devices and more particularly to an exhalation evacuation system for removing exhaled gases of a patient at medical institutions and the like.

The unrestricted exhalation into the environment from persons suffering from infectious diseases is a substantial source of contamination of persons or objects in the surrounding area. Although such problems are inherent in any social situation, the possibility of contamination or infection from a person undergoing critical care in a medical facility is particularly acute. Studies have determined that a not insubstantial number of nosocomial infections occur in persons receiving treatment at such facilities. Medical facilities generally practice relatively stringent infection control procedures. However, when critical care patients are placed on respiratory ventilator units bacteria and other infectious agents present in the patient's exhalation travel a substantial distance from the exhalation outlets of the unit. Such infectious contaminates pose a substantial health risk for other patients, medical personnel, and visitors.

Exemplary of the medical profession's recognition of such contamination problems are: Dyer & Peterson, *How Far do Bacteria Travel from the Exhalation Valve of IPPB Equipment?*, 51 Anesthesia and Analgesia, July-Aug. p. 516 (1972); Flournoy, Plumlee & Steffee, *Volume Ventilator as a Vehicle of Airborne Bacterial Contamination from Patients,* 25 Respiratory Care July, p. 742 (1980); Duberstein & Howard, *Sterile Filtration of Gases: A Bacterial Aerosol Challenge Test,* 32 Journal of the Parenteral Drug Ass. July-Aug., p. 192 (1978); and Irwin et al., *An Outbreak of Acinetobacter Infection Associated with the User of a Ventilator Spirometer,* 25 Respiratory Care Feb., p. 232 (1980).

Most ventilator units include an expiratory system or line consisting of a flexible tube that extends away from the patient for dispersion of the exhaled gases. Heretofore, the dispersion of contaminates in gases from the expiratory system has been reduced by the use of bacterial filters. Such filters are placed directly in the path of air flow in order to remove the majority of bacterial infectious agents that would otherwise be exhaled directly into the surrounding room. The unit may include other components in the expiratory line downstream of the filter, such as a conventional spirometer, or a conventional check valve that permits gas flow out of the line but which prevents atmospheric return back through the line while the patient is inhaling.

Problems associated with systems having a bacterial filter placed directly in the expiratory system air flow include their cost and service life. The expected service life of a filter in continuous use is approximately two days before replacement and disposal. Although a single filter is relatively inexpensive as a single component, over the period of time that a ventilation unit may be used the cost of constantly replacing the filters may be substantial.

Another problem associated with such systems is the accumulation of moisture within the filter media. Water accumulation increases the resistance of the filter to gas flow with a resulting increase in undesirable back pressure against the patient. This accumulation also reduces the effectiveness of the filter. In an attempt to reduce this moisture problem, such systems often provide a water trap in the expiratory line upstream of the bacterial filter.

Another approach previously used to reduce ventilator unit contamination is the use of a suction or vacuum for the partial recovery of exhaled gases. Most hospitals have a contained vacuum system that extends through the walls or floor of the building. The system provides a ready vacuum source necessary for various medical activities. This wall vacuum system has been used for the partial recovery of exhaled gases. In such systems it is mandatory to keep the system open, both to prevent the wall suction from evacuating the patient and to prevent a back pressure from occurring in the expiratory line against which the patient must exhale. Such an evacuation would be counter-productive to ventilation and might pose a substantial hazard for the patient. Since the system must remain open, infectious contaminates may escape from the system and pass unrestrained into the surrounding room. This condition may occur quite frequently in such a system since the force of exhalation varies during the cycle of a single breath.

There is a substantial need, therefore, for a contained system for treating exhaled gases emitted from respiratory ventilator units or the like. Due to the length of time that use of such a unit may be necessary, it would be highly desirable to provide such a unit with components that do not require frequent replacement in order to reduce re-occurring costs.

SUMMARY OF THE INVENTION

The present invention solves the problems noted above by the provision of a contamination control device for use with respiratory ventilator units or the like and that provides a closed system for disposal of exhaled gases through a hospital's existing vacuum supply lines. The closed system does not normally require the continuous filtering of the exhaled gases, and under normal conditions reduces the dispersement of exhaled gases into the surrounding area to virtually zero. The closed system provides for the containment of exhaled contaminates without posing the hazard of evacuating the patient or producing an undesirable back pressure against exhalation by the patient.

Preferably, the invention includes a chamber having an inlet coupled to the expiratory line of the ventilator unit. A flexible collection bag is mounted on the chamber, and the outlet of the chamber is coupled to the contained vacuum system normally present in hospitals or other medical facilities. A one-way check valve between the chamber and the surrounding atmosphere prevents exhaled gases from escaping outwardly to the surrounding room, but permits gas flow inwardly from the atmosphere to the chamber. As the patient exhales the flexible collection bag temporarily stores gas in excess of that which the vacuum source can handle, while the one-way check valve prevents the vacuum source from evacuating the patient, such as during inhalation. The system also preferably includes a bacteria filter that filters and vents the chamber to the surrounding atmosphere in the event that the vacuum source fails, and an audible signal is emitted upon such failure.

It will be recognized that the control device reduces the potential for contamination through patient exhalation under normal operation, and even in the event of a failure of the vacuum system the exhaled gases are filtered prior to venting to the atmosphere. Since the control device does not require the constant direct filtering of the exhaled gases, frequent replacement of components is not required. The cost of use of the device is therefore substantially less than other systems having frequently replaced non-reusable filters. The device reduces hospital costs by decreasing the length of patient stay resulting from nosocomial infections and by decreasing the incidence of employee illness and resulting decreases in efficiency and increased sick leave.

These and other objects, features, results and advantages of the invention will be recognized from the specification, claims and drawings filed herewith.

DETAILED DESCRIPTION OF THE PREFERRED EMBODIMENT

Figure 1:
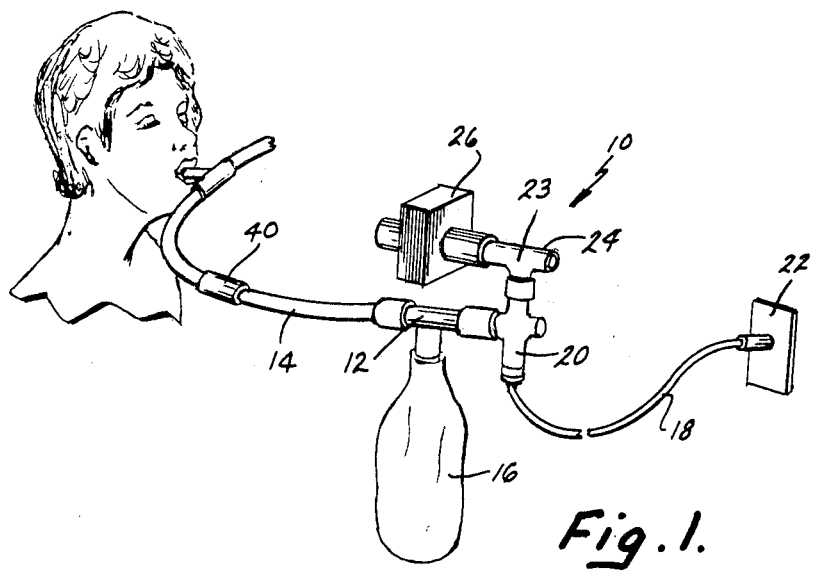
FIG. 1 is a fragmentary, perspective view of the ventilator contamination control device in accordance with the present invention connected to a respiratory ventilator unit and a vacuum source.
Figure 2:
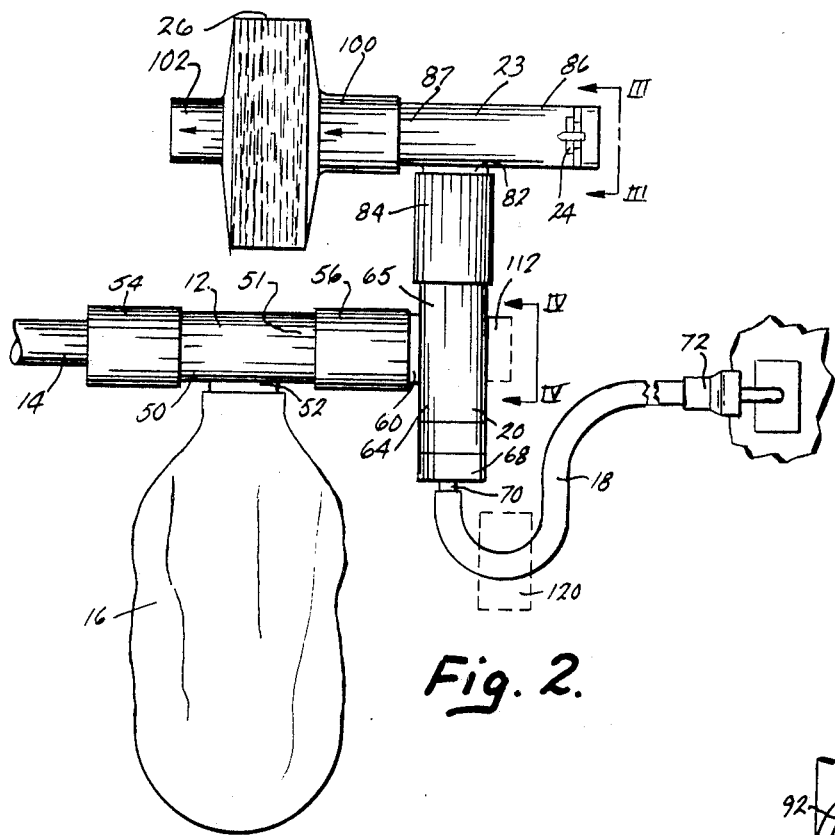
FIG. 2 is a fragmentary, side view schematic diagram of the ventilator contamination control device shown in FIG. 1.

The preferred embodiment of a control device in accordance with the present invention is shown in FIGS. 1 and 2 and generally designated by the numeral 10. Device 10 includes an inlet tube 12 which is coupled to an expiratory line 14 of a conventional respiratory ventilator unit. A flexible containment bag or container 16 depends from tube 12. Bag 16 temporarily retains excess exhaled gases during the respiration cycle. A connecting hose 18 couples an outlet tube 20 to a conventional contained vacuum source 22. An upper mounting tube 23 mounts a unidirectional check valve 24 on outlet tube 20. Check valve 24 permits the inflow of atmospheric gases to tubes 12 and 20, but prevents the escape of exhaled gases to the atmosphere. A bacteria filter unit 26, also mounted on tube 23, provides a filtered vent to the atmosphere from tubes 12 and 20.

Contamination control device 10 provides a closed exhalation system, in that under normal conditions tubes 12, 20 and 23 form an air impermeable chamber or housing through which exhaled gases pass from expiratory line 14 to contained vacuum source 22. Device 10 does not permit open, unfiltered flow of exhaled gases from expiratory line 14 to the atmosphere, and does not require the exhales gases to pass through a filter under normal operation. Although filter unit 26 provides a filtered vent to the atmosphere, filter unit 26 maintains the "closed" system that prevents the escape of contaminates even in the event of a failure of the hospital's vacuum system or the like.

Expiratory line 14 is a conventional flexible hose that conveys exhaled gases away from a patient during use of a conventional respiratory ventilator unit. Preferably expiratory line 14 includes a one-way check valve 40 that permits the passage of exhaled gases outwardly through line 14, but which prevents the backflow of gases through line 14.

Tube 12 is a T-shaped, hollow tubular cylindrical joint having aligned branches or legs 50 and 51, and a depending branch or leg 52. Tube 12 is made of a gas impermeable polymeric material and is preferably at least semi-transparent to permit visual inspection for obstructions or contaminates. Inlet branch 50 and outlet branch 51 are coupled to expiratory line 14 and to outlet tube 20, respectively, by means of a pair of coupling collars 54 and 56. Collars 54 and 56 are cylindrical tubes and are also made of a polymeric material friction fit to the elements to be joined, in order to provide a gas impermeable seal therebetween but communication between the joined elements. Branches 50–52 each preferably have an outside diameter of twenty-two millimeters. A suitable inlet tube 12, as well as outlet tube 20 and mounting tube 23, are marketed by Air Life Inc., a subsidiary of American Hospital Supply Corp., a company of Montclair, California.

Depending branch or leg 54 provides a mounting port for containment bag 16. Containment bag 16 is a conventional flexible bag manufactured from a gas impermeable material, such as a polymeric or rubber compound. Bag 16 is sealed on branch 54 in a conventional manner, such as by a sealing adhesive, tape or the like in order to provide a gas impermeable seal therebetween. Bag 16 provides an expandable containment vessel for the overflow control of exhaled gases by its expansion and temporary containment of gases in excess of those evacuable by vacuum source 22. Bag 16 is evacuated by vacuum source 22, rather than by return of exhaled gases back up through expiratory line 14. Check valve 40 insures the evacuation of bag 16 by vacuum source 22. In ventilator units not including an expiratory line check valve 14, a removable check valve element may be coupled between expiratory line 14 and inlet branch 50 of tube 12 in a conventional fashion.

Outlet tube 20 has a generally cross shaped configuration, with a branch or leg 60 connected to branch 51 of tube 12. Tube 20 also includes a depending branch 64 and an upwardly extending branch 65. Tube 20 is preferably made from a polymeric material and branches 60, 64 and 65 have an outside diameter of twenty-two millimeters. Connecting hose 18 is coupled to depending branch 64 by a reduction plug 68. Reduction plug 68 is press fit into branch 64 and has a nipple 70 over which connecting hose 18 is fitted, thereby forming a friction seal. On the opposite end of connecting hose 18 is a female connector 72. Connector 72 is removably fitted over the male outlet for vacuum source 22. Connecting hose 18 is a flexible, polymeric hose that is most preferably at least semi-transparent to permit visual inspection. Vacuum source 22 may be of any conventional type normally found in hospitals and the like. Such vacuum sources typically include a network of piping extending through the walls of the hospital that lead to a common vacuum pump.

Upwardly extending branch 65 is connected to upper mounting tube 23 in order to be in air flow communication therewith. Mounting tube 23 has an overall T-shape, with a depending branch or leg 82 that is connected and sealed to branch 65 of tube 20 by a collar 84. Collar 84 is similar in structure to collars 54 and 56. Upper mounting tube 23 has a pair of opposed mounting branches 86 and 87 which are used for mounting check valve 24 and filter unit 26, respectively.

Figure 3:
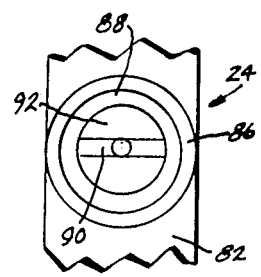
FIG. 3 is a fragmentary, end view of the one-way check valve used in the device taken along plane III—III of FIG. 2.

As best shown in FIG. 3, check valve 24 is a flapper-type valve that provides inward gas flow from the surrounding atmosphere through branch 86, but prevents flow outwardly from tube 23 to the atmosphere. Check valve 23 has a conventional structure that includes an annular lip 88 within branch 86, and a cross piece 90 on which a flapper element 92 is mounted. Flapper element 92 is a readily flexible, gas impermeable membrane that in a closed condition lies in abutment with annular lip 88. A positive pressure within tube 23 forces flapper element 92 into a closed condition, but a negative pressure within tube 23 causes flapper element 92 to flex inwardly to provide an inward air flow. Flapper element 92 may be made of various impermeable materials, but must be sufficiently flexible to provide a lower resistance to the inward flow of air than the resistance provided by the combination of chamber 12 in connection with expiratory line 14. The flow resistance of check valve 24 may be varied according to the flow resistance of expiratory line 14, but the preferable range of inward flow resistance of valve 24 is less than approximately 0.9 centimeters of water column pressure, and most preferably is in the range of approximately 0.5 centimeters of water or less. One suitable check valve is marketed by Air Life Ince., a subsidary of American Hospital Supply Corp., Montclair, Calif. 91763, and identified as a one-way internal valve.

Filter unit 26 includes a cylindrical mounting inlet 100 which is friction fit onto branch 87 in order to seal thereon. Opening opposite inlet 100 is outlet 102 that vents to atmosphere. Filter unit 26 includes a conventional bacteria filter media that provides a low resistance to air flow. Preferably, filter 26 provides a flow resistance of less than 0.9 centimeters of water at 50 liters per minute of flow. One such suitable bacteria filter is marketed by Pall Biomedical Products Corporation of Eash Hills, N.Y. 11548 under the trade name PALL BREATHING CIRCUIT FILTER. Branch 87 and filter unit 26 provide a failure circuit that permits normal exhalation through the ventilator unit in the event of failure of vacuum source 22, blockage of hose 18 or the like, while still providing filtration of the exhaled gases. Additionally, filter unit 26 provides a secondary inlet in the event that check valve 24 fails. In such an instance, vacuum source 22 will draw atmospheric air in through filter unit 26, rather than causing an evacuation of the patient circuit.

Figure 4:
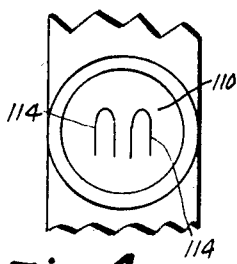
FIG. 4 is a fragmentary, end view of the audible signal device used in the ventilation contamination control device taken along plane IV—IV of FIG. 2.

In an alternative embodiment shown in phantom in FIG. 4, a reed valve 110 is mounted in a branch 112 of tube 20 opposite connecting branch 60. Reed valve 110 provides an audible altering signal when either the evacuating vacuum source 22 or inlet check valve 24 fails. Reed valve 110 has two reeds 114, one reed responding to an inward flow of air and the other responding to an outward flow. Under normal operating conditions reeds 114 maintain valve 110 in a substantially closed condition so that contaminates do not escape through valve 110. Reed valve 110 responds to an air flow pressure slightly less than the air flow resistance of filter 26, so that valve 110 produces an audible signal at the point at which air is passing through filter 26. A bacteria filter media 113 similar to that of filter unit 26 is located in branch 112 either upstream or downstream of reed valve 110 to prevent contaminants from escaping through valve 110. If the vacuum source draws gases from the patient due to blockage of valve 24 and/or filter 26, air will be drawn in through valve 110 also sounding an alarm. Additionally, connecting hose 18 may alternatively include a water trap assembly 120 of conventional design. Water trap 120 collects moisture collecting within the housing formed by tubes 12, 20 and 23.

It will be noted that although inlet tube 12, outlet tube 20 and upper mounting tube 80 are separate elements, these separate components could be manufactured as a single unit in order to provide a unitary, gas impermeable housing to which the other components are secured.

It is to be realized that the above is merely a description of the preferred embodiment, and it will be recognized by one skilled in the art that various modifications or improvements may be made to the preferred embodiment without departing from the spirit of the invention disclosed herein. The scope of the protection afforded is to be determined by the claims which follow and the breadth of interpretation which the law allows.

The embodiments of the invention in which an exclusive property or privilege is claimed are defined as follows.

1. An exhalation evacuation device for use with a ventilation unit to remove exhaled gases from a patient through a vacuum source, said device comprising:
   a housing defining an exhalation inlet connectable to the ventilation unit, a channel extending from said exhalation inlet through said housing to an exhalation outlet connectable to a vacuum source, an atmospheric inlet in gas flow communication with said channel, a filter port in gas flow communication with said channel and providing a filter outlet from said housing separate from said exhalation outlet;
   a check valve mounted at said atmospheric inlet for permitting flow of air into said housing; and
   a bacteria filter mounted at said filter port.

2. An exhalation evacuation device as defined by claim 1 wherein said bacteria filter has a gas flow resistance greater than the inward gas flow resistance of said check valve.

3. The exhalation evacuation device of claim 1, further comprising:
   an excess gas port on said housing in gas flow communication with said channel; and
   an excess gas collection container mounted at said excess gas port.

4. An exhalation evacuation device as defined by claim 3, wherein said container is a bag.

5. An exhalation evacuation device for use with a ventilation unit to remove exhaled gases from a patient through a vacuum source, said device comprising:
   a housing defining an exhalation inlet connectable to the ventilation unit, a channel extending from said exhalation inlet through said housing to an exhalation outlet connectable to a vacuum source, an atmospheric inlet in gas flow communication with said channel, a filter port in gas flow communication with said channel and providing a filter outlet from said housing separate from said exhalation outlet and an excess gas port in gas flow communication with said channel;
   a check valve mounted at said atmospheric inlet for permitting flow of air into said housing;
   a bacteria filter mounted at said filter port for filtering exhaled gases passing through said filter port in the event of failure of the vacuum source, said bacteria filter having a gas flow resistance greater than the inward gas flow resistance of said check valve;
   an excess gas collection container mounted at said excess gas port; and an audible alarm means on said housing for generating an alarm when exhaled gases pass through said filter.

6. An exhalation evacuation device for use with a ventilation unit to remove exhaled gases from a patient through a vacuum source, said device comprising:
 a housing defining an exhalation inlet connectable to the ventilation unit, a channel extending from said exhalation inlet through said housing to an exhalation outlet connectable to a vacuum source, an atmospheric inlet in gas flow communication with said channel, a filter port in gas flow communication with said channel and providing a filter outlet from said housing separate from said exhalation outlet and an excess gas port in gas flow communication with said channel;
 a check valve mounted at said atmospheric inlet for permitting flow of air into said housing;
 a bacteria filter mounted at said filter port for filtering exhaled gases passing through said filter port in the vent of failure of the vacuum source, said bacteria filter having a gas flow resistance greater than the inward gas flow resistance of said check valve;
 an excess gas collection container mounted at said excess gas port; and
 an audible alarm means on said housing for generating an alarm when the vacuum source draws gases from the ventilation unit due to blockage of the atmospheric inlet and the filter port.

7. An exhalation evacuation device as defined by claim 6 wherein said audible alarm means generates an alarm when exhaled gases flow through said filter port.

8. A ventilation contamination control device for use in the containment of human exhalation from a respiratory ventilator unit for disposal through a contained vacuum system, comprising:
 an air impermeable housing having a gas flow channel extending between an exhalation inlet and an exhalation outlet, said inlet having means for operable connection to the exhalation output of a respiratory ventilator unit;
 said exhalation outlet having means for operable connection to a contained vacuum source so as to evacuate exhaled gases from said housing through said contained vacuum source;
 an atmospheric inlet port on said housing in communication with said gas flow channel, said atmospheric inlet port having an unidirectional valve therein, said unidirectional valve providing gas flow from the atmosphere inwardly through said atmospheric inlet port to said housing, but preventing gas flow from said housing outwardly through said atmospheric inlet port to the atmosphere, said unidirectional valve providing less resistance to inward gas flow than the gas flow resistance of said housing in connection with a respiratory ventilator unit;
 a filter outlet port on said housing in communication with said gas flow channel and with said exhalation inlet therethrough, said filter outlet port providing a filter outlet separate from said exhalation outlet; and
 a bacteria filter mounted on said filter outlet port, said bacteria filter having a gas flow resistance greater than the inward gas flow resistance of said unidirectional valve, whereby said device provides a closed exhalation containment system in which gases exhaled through said respiratory ventilator unit pass through said exhalation inlet and are evacuated through said exhalation outlet to said contained vacuum source, and said unidirectional valve provides an inflow of gas when the rate of gas evacuation by said contained vacuum source exceeds exhalation so that said device does not evacuate the patient or provide a substantial back pressure against exhalation.

9. The exhalation evacuation device of claim 8, further comprising:
 an overflow control port on said housing in communication with said gas flow channel and having an exhalation overflow retention bag mounted thereon.

10. A ventilation contamination control device for use in the containment of human exhalation from a respiratory ventilator unit for disposal through a contained vacuum system, comprising:
 an air impermeable housing having a gas flow channel extending between an exhalation inlet and an exhalation outlet, said inlet having means for operable connection to the exhalation output of a respiratory ventilator unit;
 said housing including an overflow control port in communication with said gas flow channel and having an exhalation overflow retention bag mounted thereon;
 said exhalation outlet having means for operable connection to a contained vacuum source so as to evacuate exhaled gases from said housing and said retention bag through said contained vacuum source;
 an atmospheric inlet port on said housing in communication with said gas flow channel, said atmospheric inlet port having an unidirectional valve therein, said unidirectional valve providing gas flow from the atmosphere inwardly through said atmospheric inlet port to said housing, but preventing gas flow from said housing outwardly through said atmospheric inlet port to the atmosphere, said unidirectional valve providing less resistance to inward gas flow than the gas flow resistance of said housing in connection with a respiratory ventilator unit;
 a filter outlet port on said housing and communicating with said exhalation inlet;
 a bacteria filter mounted on said filter outlet port, said bacteria filter having a gas flow resistance greater than the inward gas flow resistance of said unidirectional valve; and
 means for providing an audible signal when exhaled gases pass through said bacteria filter, said audible signal means preventing substantial gas flow therethrough when not providing said audible signal, whereby said device provides a closed exhalation containment system in which gases exhaled through said respiratory ventilator unit pass through said exhalation inlet and are evacuated through said exhalation outlet to said contained vacuum source, said overflow retention bag temporarily containing exhaled gases in excess of the rate of gas evacuation of said contained vacuum source, and said unidirectional valve providing an inflow of gas when the rate of gas evacuation by said contained vacuum source exceeds exhalation so that said device does not evacuate the patient or provide a substantial back pressure against exhalation.

11. A ventilation contamination control device for use in the coupling of the expiratory circuit of a ventilator unit to a closed vacuum system, comprising:

an exhalation chamber having an inlet with means for coupling said chamber to said expiratory circuit of said ventilator unit for contained gas flow therebetween;

a flexible exhalation containment bag depending from said exhalation inlet chamber and providing for contained gas flow therebetween;

said exhalation chamber having an outlet tube extending therefrom, said outlet tube having means for communicating said tube to said closed vacuum system, and said exhalation chamber having a filter outlet separate from said tube communicating means;

a check valve on said exhalation chamber providing inward gas flow from the atmosphere into said exhalation chamber, but preventing outward gas flow from said exhalation chamber to the atmosphere, said check valve having an inward gas flow resistance less than the gas flow resistance of said exhalation chamber coupled to said expiratory circuit of said ventilator unit; and a bacteria filter unit secured on said filter outlet of said exhalation chamber to provide gas flow therebetween and vent said exhalation chamber therethrough, said bacteria filter unit providing a greater gas flow resistance than the inward gas flow resistance of said check valve, whereby said device provides a normally closed exhalation containment system, but said bacteria filter unit provides filtered emission of exhaled gases upon failure of said closed vacuum system.

12. A ventilation contamination control device for use in the coupling of the expiratory circuit of a ventilator unit to a closed vacuum system, comprising:

an exhalation chamber having an inlet with means for coupling said chamber to said expiratory circuit of said ventilator unit for contained gas flow therebetween;

a flexible exhalation containment bag depending from said exhalation inlet chamber and providing for contained gas flow therebetween;

said exhalation chamber having an outlet tube extending therefrom, said outlet tube having means for communicating said tube to said closed vacuum system;

a check valve on said exhalation chamber providing inward gas flow from the atmosphere into said exhalation chamber, but preventing outward gas flow from said exhalation chamber to the atmosphere, said check valve having an inward gas flow resistance less than the gas flow resistance of said exhalation chamber coupled to said expiratory circuit of said ventilator unit;

a bacteria filter unit secured on said exhalation chamber to provide gas flow therebetween and vent said exhalation chamber therethrough, said bacteria filter unit providing a greater gas flow resistance than the inward gas flow resistance of said check valve; and means for providing an audible signal when exhaled gases pass through said bacteria filter, said audible signal means preventing substantial gas flow therethrough when not providing said audible signal, whereby said device provides a normally closed exhalation containment system, but said bacteria filter unit provides filtered emission of exhaled gases upon failure of said closed vacuum system.

13. A ventilator unit contamination control device, comprising:

an exhalation chamber having an inlet with means for operable connection to the exhalation output of a respiratory ventilator unit, and having an outlet with means for coupling to a contained vacuum system;

an atmospheric inlet port on said exhalation chamber, said inlet port having a check valve therein that provides inward gas flow therethrough from the atmosphere into said exhalation chamber, but which prevents outward gas flow therethrough from said exhalation chamber to the atmosphere; and said exhalation chamber including a vent to atmosphere, said vent having a bacteria filter therein, said bacteria filter providing a gas flow resistance greater than the inward gas flow resistance of said check valve, whereby respiratory gases exhaled through said ventilator unit pass through said exhalation chamber and are evacuated to said contained vacuum source, and said check valve provides an inflow of gas when the rate of gas evacuation by said contained vacuum source exceeds gas exhalation.

14. The ventilator unit contamination control device of claim 13, further comprising:

an expandable containment vessel coupled with said exhalation chamber for contained gas flow therebetween, said expandable containment vessel temporarily containing gases exhaled to said exhalation chamber in excess of the rate of gas evacuation of said contained vacuum source.

* * * * *